US012735376B2

(12) United States Patent
Lu et al.

(10) Patent No.: US 12,735,376 B2
(45) Date of Patent: Sep. 15, 2026

(54) PREPARATION METHOD FOR METHYLPHENOL AND HOMOLOGUE

(71) Applicant: DALIAN UNIVERSITY OF TECHNOLOGY, Dalian (CN)

(72) Inventors: Anhui Lu, Dalian (CN); Kaiyuan Liu, Dalian (CN); Wencui Li, Dalian (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 450 days.

(21) Appl. No.: 18/681,697

(22) PCT Filed: Apr. 14, 2023

(86) PCT No.: PCT/CN2023/088278
§ 371 (c)(1),
(2) Date: Feb. 6, 2024

(87) PCT Pub. No.: WO2024/212204
PCT Pub. Date: Oct. 17, 2024

(65) Prior Publication Data

US 2025/0223251 A1 Jul. 10, 2025

(51) Int. Cl.
*C07C 37/20* (2006.01)
*B01J 27/18* (2006.01)
(Continued)

(52) U.S. Cl.
CPC ........... *C07C 37/20* (2013.01); *B01J 27/1806* (2013.01); *B01J 27/1813* (2013.01);
(Continued)

(58) Field of Classification Search
None
See application file for complete search history.

(56) References Cited

FOREIGN PATENT DOCUMENTS

| | | |
|---|---|---|
| CN | 109111343 A | 1/2019 |
| CN | 109111345 A | 1/2019 |

(Continued)

OTHER PUBLICATIONS

English translation of Huang et al. (CN 112225645, pub date Jan. 15, 2021) (Year: 2021).*

(Continued)

*Primary Examiner* — Renee Claytor
*Assistant Examiner* — Jennifer C Sawyer
(74) *Attorney, Agent, or Firm* — MUNCY, GEISSLER, OLDS & LOWE, P.C.

(57) ABSTRACT

A preparation method for methylphenol and homologue. Under the conditions of reaction temperature of 150-350° C. and reaction pressure of 1-50 atm, a mixed material of methanol, ethanol and acetone is fed into a reactor containing a catalyst by a carrier gas to produce methylphenol through coupling-aromatization reaction. The method provides a reaction path for directly producing methylphenol and homologue from low carbon micromolecular alcohol and ketone through coupling-aromatization reaction, the maximum selectivity of total cresol is 34.0%, and the selectivity of 2,3,6-trimethylphenol is up to 7.1%. The by-product hydrogen of the reaction path can be used as a chemical material. Other by-products such as high carbon alcohol and ketone whose melting and boiling points are quite different from those of methylphenol and which are easy to be separated by rectification can be used as fuel additives to partially replace petroleum-based products.

10 Claims, 1 Drawing Sheet

(51) Int. Cl.
*B01J 37/00* (2006.01)
*B01J 37/04* (2006.01)
*B01J 37/10* (2006.01)
*B01J 37/18* (2006.01)

(52) U.S. Cl.
CPC ......... *B01J 27/1817* (2013.01); *B01J 37/009* (2013.01); *B01J 37/04* (2013.01); *B01J 37/10* (2013.01); *B01J 37/18* (2013.01)

(56) References Cited

FOREIGN PATENT DOCUMENTS

| | | | |
|---|---|---|---|
| CN | 112225645 | A | 1/2021 |
| WO | WO-2016/172771 | A1 | 11/2016 |
| WO | WO-2023/010390 | A1 | 2/2023 |

OTHER PUBLICATIONS

Zhou, B. "Enhancing Ethanol Coupling to Produce Higher Alcohols by Tuning H2 Partial Pressure over a Copper—Hydroxyapatite Catalyst", ACS Catal., 12, (Sep. 21, 2022), pp. 12045-12054, ISSN: 2155-5435.

Ho.C.R., "The Mechanism and Kinetics of Methyl Isobutyl Ketone Synthesis from Acetone over Ion-exchanged Hydroyapatite", J.Catal., 365, (Apr. 18, 2018), pp. 174-183, ISSN: 0021-9517 https://doi.org/10.1016/l.jcat.2018.07.005.

* cited by examiner

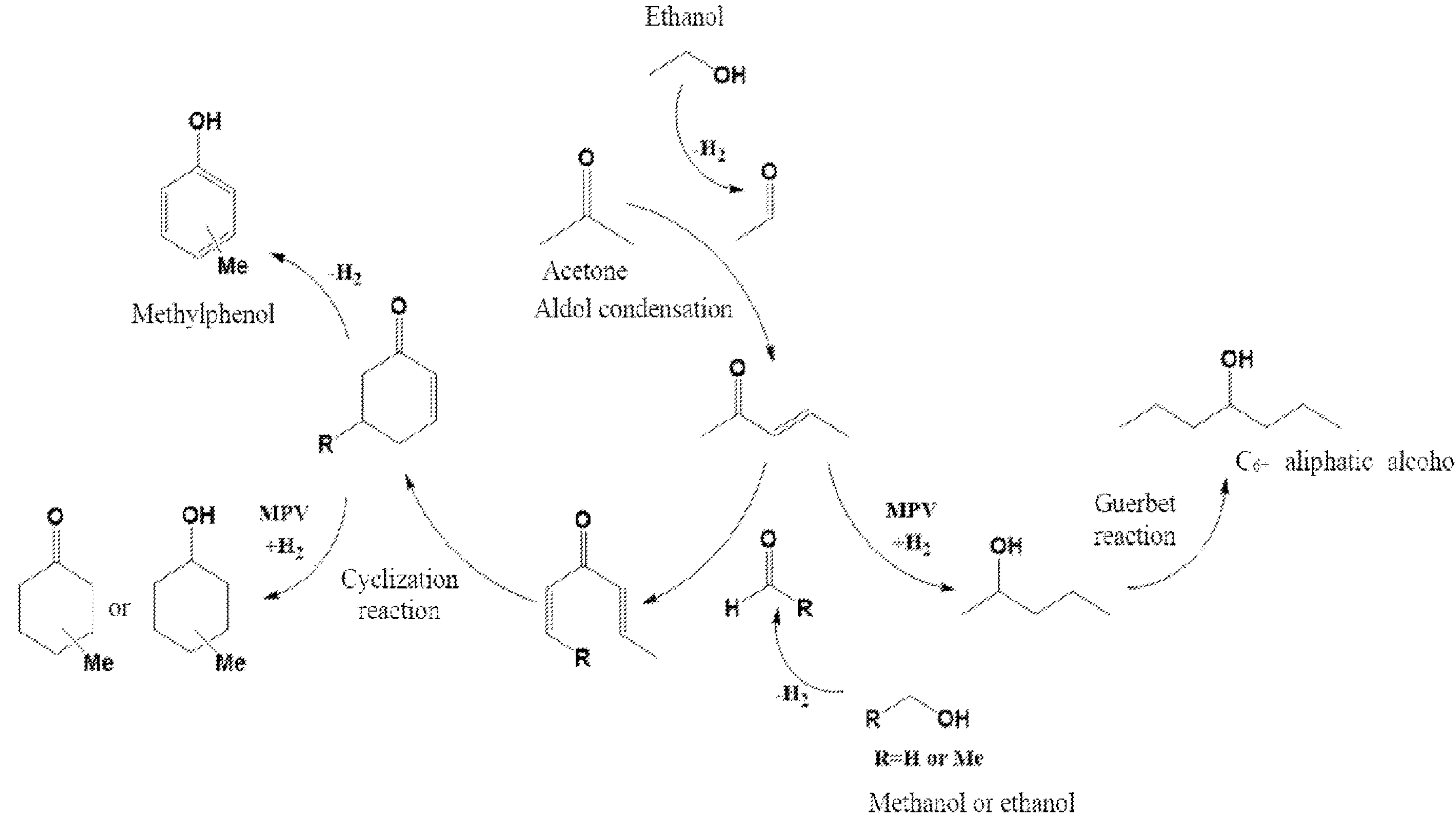
Ethanol
$-H_2$
Acetone
Aldol condensation
$-H_2$
Methylphenol
MPV
$+H_2$
Guerbet reaction
$C_{6+}$ aliphatic alcohol
MPV
$+H_2$
Cyclization reaction
or
$-H_2$
R=H or Me
Methanol or ethanol

PREPARATION METHOD FOR METHYLPHENOL AND HOMOLOGUE

TECHNICAL FIELD

The present invention relates to a method for preparing methylphenol and homologue by catalytic conversion of low carbon alcohol ketone, in particular to a method for preparing methylphenol and homologue from methanol, ethanol and acetone as reactants, and belongs to the technical field of chemical catalysis.

BACKGROUND

Methylphenol (cresol for short) and homologue are indispensable raw materials in chemical production, and are widely used in many fields such as medicine, dye, pesticide, resin and paint. M-cresol is a raw material for synthesis of a pesticide permethrin, 2,5-dimethylphenol is a flavoring agent and also a raw material for production of the drug Gemfibrozil, and 2,3,6-trimethylphenol is an essential substrate for synthesis of vitamin E.

At present, main production methods for cresol include coal tar extraction, isopropyltoluene oxidation and direct aromatics oxidation, wherein isopropyltoluene oxidation is currently the main method for producing methylphenol in the industry. Since isopropyltoluene isopropyl peroxide (tertiary CHP) is obtained by means of catalytic oxidation in the method, and both isopropyl and methyl of isopropyltoluene are likely to be oxidized, a mixture of tertiary CHP and isopropyltoluene methyl peroxide (primary CHP) is generally obtained in the oxidation step of the method. Tertiary CHP will produce cresol and acetone in the acid hydrolysis step, and primary CHP will produce isopropyl phenol and formaldehyde in the acid hydrolysis step, while formaldehyde can form a resinous substance which is difficult to handle with phenolic substances, and consume the target product cresol, resulting in reduced selectivity [Petrochemical Industry Trends, 1993, 3, 39-42]. High carbon phenol such as 2,3,6-trimethylphenol and 2,3,5-trimethylphenol is produced by methylation of cresol and obtained by reaction of cresol and methanol under catalysis, and while the substrate depends on the cresol production route, the reaction path needs to be obtained by two-step reaction [CN102976903A], so the cost is high. Isopropyltoluene in the cumene oxidation route is obtained by hydrocarbylation reaction of petroleum products toluene and propylene, and arene materials are in shortage due to increasing focus of refineries on the production of light gasoline [*Science* 2014, 344, 616; *Angew. Chem. Int. Ed.* 2013, 52, 11980]. For the above routes, methylphenol and homologue are obtained by oxidation of arene materials.

In recent years, high-value conversion and utilization of low carbon resources has attracted wide attention. The preparation of high carbon alcohol [*ACS Catal.* 2022, 12, 12045-12054], high carbon ketone [*Angew Chem Int Ed.* 2020, 59(34): 14550-14557] and aromatic alcohol [U.S. Pat. Nos. 10,960,386 B2, 11,338,275 B2] from ethanol has been reported. In addition, the conversion from ethanol to phenolic products has been sporadically reported, for example, with hydrotalcite as a catalyst, the selectivity of phenolic products obtained by ethanol conversion is 35% at high temperature of 450° C. [*Catalysis Today.* 2016, 269 (1):82-87]; and with $Ce(OH)SO_4 \cdot xH_2O$ as a catalyst, ethanol can be converted into phenolic products at 420° C. and at low space velocity <10 $min^{-1}$ [*ACS Catal.* 2021, 11, 6162-6174]. In the above reports, ethanol is used as a single reactant to produce phenolic products through a path of rearrangement, condensation and aromatization at high temperature of 400-450° C., which results in a large number of alkene by-products in the products.

A new way for preparing methylphenol and homologue from methanol, ethanol and acetone through a path of cross coupling-aromatization is developed. The route is highly innovative, which can expand a new way of green production of fine chemicals and realize the high-value comprehensive utilization of low carbon micromolecules.

SUMMARY

The purpose of the present invention is to provide a route for preparing methylphenol and homologue from methanol, ethanol and acetone as reactants through dehydrogenation-cross coupling-aromatization reaction and to provide a catalyst required for the catalytic conversion route, which is specially emphasized to be the first reported synthesis route of methylphenol and homologue, with notable creativity. The route has the most important characteristic that target products methylphenol and homologue are produced with a catalyst at low temperature (≤300° C.) in one step, which is a new green route to produce methylphenol and homologue and meets the needs of energy conservation, consumption reduction and sustainable development strategies.

The reaction network of a preparation method for methylphenol and homologue is as follows:

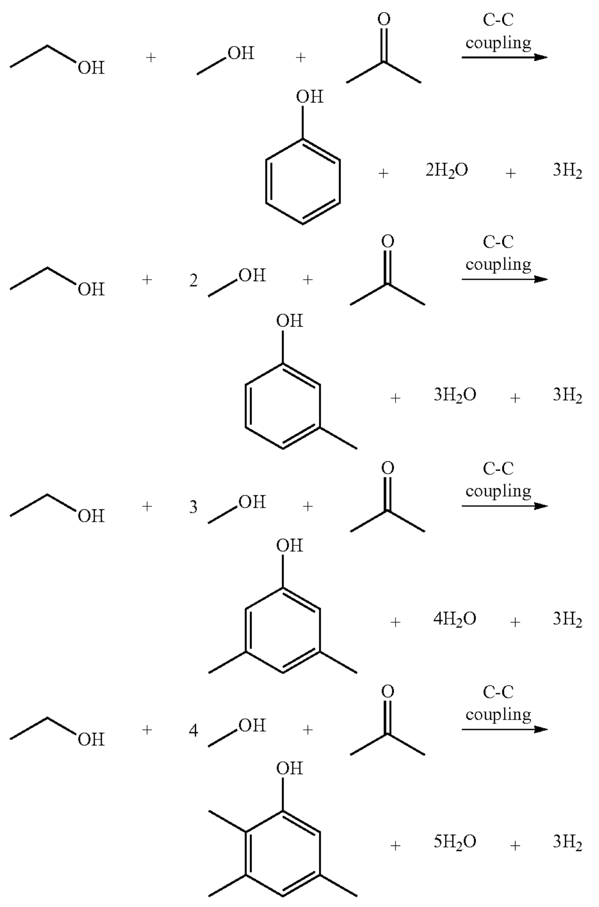

The present invention creatively proposes use of three low carbon molecules as reactants for production of methylphenol and homologue through a new reaction path. The synthesis of cresol and homologue by catalytic conversion of low carbon micromolecules has the advantages of less pollution, less three wastes and easy product separation, and avoids use of petroleum-based raw materials. The reaction temperature of the reaction path is low, the selectivity of total cresol is up to 34.0%, and the selectivity of 2,3,6-trimethylphenol is up to 7.1%, with a good industrial application prospect. The innovation points of this patent include innovation of the reaction path and innovation of the catalyst system.

The technical solution of the present invention is as follows:

A preparation method for methylphenol and homologue comprises the following steps:

Under the conditions of reaction temperature of 150-350° C. and reaction pressure of 1-50 atm, a mixed material of methanol, ethanol and acetone is fed into a reactor containing a catalyst by a carrier gas at the total flow of the reaction gas of 20-200 mL/min to produce methylphenol through coupling-aromatization reaction.

The ranges of partial pressures of the reactants methanol, ethanol and acetone are respectively 0.1-10 kPa, and the ratio of partial pressures of methanol, ethanol and acetone is (0.5-40):(0.5-40):1 and preferably (0.5-15):(0.5-15):1. The total flow of the reaction gas is preferably 30 mL/min.

The reactor is preferably a fix bed reactor and a normal pressure reactor.

The weight hourly space velocity of the reaction is 0.01-3 $h^{-1}$ and preferably 0.2-1.5 $h^{-1}$.

The carrier gas is an inert gas such as nitrogen, argon and helium.

The catalyst is a hydroxyphosphate catalyst, with the chemical formula of $A_xB_yC_zD_mE_n(OH)_2(PO_4)_6$, wherein x+y+z+m+n=9-10, 9-10≥x, y, z, m, n≥0, A, B, C, D and E are the same or different, and are selected from one or a combination of more than one of Mg, Ca, Sr, Ba and Pb, and hydroxyphosphate is one or a mechanical mixture of more than one.

The hydroxyphosphate is preferably is $Ca_{10}(OH)_2(PO_4)_6$.

The catalyst is a hydroxyphosphate catalyst modified by transition metal, comprising components by weight percent; transition metal comprises non-noble metal and/or noble metal; the non-noble metal is selected from one or a combination of more than one of Co, Ni, Cu, Zn and Y; the noble metal is selected from one or a combination of more than one of Ag, Pt and Ir; the transition metal is in an oxidation state or metallic state; and nitrate, chloride, levulinate, sulfate or acetate of the metal is used as a precursor, the concentration of a precursor solution is 0.05 g/mL-0.75 g/mL, and the modification amount of the transition metal is 0.01-50 wt % of the weight of hydroxyphosphate.

The transition metal is preferably Ag and Cu, and the modification amount is 0.1-10 wt % of the hydroxyphosphate.

The hydroxyphosphate catalyst modified by transition metal is reduced for 1-5 h at 350-750° C. in hydrogen atmosphere before reaction, and the concentration of the hydrogen atmosphere is one of 5-30 vol % $H_2/N_2$, 5-30 vol % $H_2/He$ and 5-30 vol % $H_2/Ar$.

The catalyst is a mixture of a hydroxyphosphate catalyst and a hydroxyphosphate catalyst modified by transition metal.

The present invention has the following beneficial effects: compared with the prior art, the present invention provides a reaction path for directly producing methylphenol and homologue from low carbon micromolecular alcohol and ketone through coupling-aromatization reaction, the maximum selectivity of total cresol is 34.0%, and the selectivity of 2,3,6-trimethylphenol is up to 7.1%. The by-product hydrogen of the reaction path can be used as a chemical material. Other by-products such as high carbon alcohol and ketone ($C_3$-$C_8$) whose melting and boiling points are quite different from those of methylphenol and which are easy to be separated by rectification can be used as fuel additives to partially replace petroleum-based products, which provides an alternative path for synthesis of methylphenol products, has great strategic significance for energy security and has a high industrial application prospect.

DESCRIPTION OF DRAWINGS

The FIGURE shows a reaction path for producing methylphenol by coupling of methanol, ethanol and acetone proposed in the present invention, and MPV reaction is Meerwein-Ponndorf-Verley hydrogenation reaction.

DETAILED DESCRIPTION

The present invention is described below in detail through some embodiments. However, the present invention is not limited to these embodiments.

Hydroxyphosphate is represented by HAP-M, wherein HAP indicates metal hydroxyphosphate, and M indicates metal which is one or several of Mg, Ca, Sr, Ba and Pb.

Hydroxyphosphate modified by metal is represented by an xMetal-HAP-M carrier, wherein Metal indicates loaded transition metal and is one or several of non-noble metal such as Co, Ni, Cu, Zn and Y and/or noble metal such as Pt, Ag and Ir, and x is the percentage of the Metal modification amount in the total weight of the catalyst multiplied by 100.

Embodiment 1

Preparation Process for HAP-Ca Catalyst:

(1) $Ca(NO_3)_2{\cdot}xH_2O$ and $(NH_4)_2HPO_4$ are prepared into 0.5 mol/L and 0.3 mol/L aqueous solutions;

(2) The two salt solutions are mixed according to the volume ratio of 1:1 at 25° C., the pH of the mixture is adjusted to 10 with ammonia, and the mixture is stirred and mixed with a magnetic stirrer for 2 h;

(3) The mixture obtained by stirring in step (2) is kept reacting for 24 h in a 80° C. homogeneous reactor or hydrothermal device for 24 h;

(4) The sediment obtained in step (3) is filtered, and dried at 100° C., and the obtained precursor is roasted in air atmosphere at 600° C. for 2 h to obtain the HAP-Ca catalyst which corresponds to No. 1 in Table 1;

(5) Different HAP-Ms can be prepared by controlling the type of metal (one or several of Mg, Ca, Sr, Ba and Pb) in the nitrate solution in the same method as the above steps.

The preparation conditions and process of other catalysts are the same as those in embodiment 1. The corresponding relation between sample numbers and preparation conditions is shown in Table 1.

TABLE 1

Corresponding Relation between Sample Numbers and Preparation Conditions in Embodiment 1

| No. | Catalyst | Metal Salt | Hydro-thermal Tempera-ture/° C. | Drying Tempera-ture/° C. | Roasting Tempera-ture/° C. |
|---|---|---|---|---|---|
| 1 | HAP-Ca | Calcium nitrate | 80 | 100 | 600 |
| 2 | HAP-Mg | Magnesium nitrate | 80 | 100 | 600 |
| 3 | HAP-Sr | Strontium nitrate | 80 | 100 | 600 |
| 4 | HAP-Ba | Barium nitrate | 80 | 100 | 600 |
| 5 | HAP-Pb | Lead nitrate | 80 | 100 | 600 |
| 6 | HAP-Ca/Sr | Calcium nitrate + strontium nitrate | 80 | 100 | 600 |

Embodiment 2

Preparation Process for HAP-Ca Catalyst Modified by Ag Species:

(1) HAP-Ca is dried in a 120° C. airflow oven for 2 h to remove physical adsorbed water on the surface;

(2) An $AgNO_3$ aqueous solution with a mass concentration of 0.05 g/mL is prepared at 25° C., and the HAP-Ca obtained by drying in step (1) is treated with an incipient-wetness impregnation method and kept standing for 2 h;

(3) The mixture obtained after standing in step (2) is dried in 50° C. air atmosphere for 10 h to obtain a catalyst precursor;

(4) The catalyst precursor obtained in step (3) is roasted in air atmosphere at 350° C. for 2 h, and then reduced in 400° C. hydrogen atmosphere for 2 h (10 vol % $H_2/N_2$) to obtain an Ag-modified HAP-Ca catalyst which is denoted as 0.1 Ag-HAP-Ca catalyst and corresponds to No. 1 in Table 2.

(5) The type and modification amount of the metal can be controlled by controlling the type, the concentration and the number of impregnations of the metal salt solution, and the preparation method is the same as the above steps.

The preparation conditions and process of other catalysts are the same as those in embodiment 2. The corresponding relation between sample numbers and preparation conditions is shown in Table 2.

TABLE 2

Corresponding Relation between Sample Numbers and Preparation Conditions in Embodiment 2

| No. | Catalyst | Metal/ wt % | Carrier | Metal Salt | Solvent | Concentration/ g $mL^{-1}$ | Reduction Temperature |
|---|---|---|---|---|---|---|---|
| 1 | 0.1Ag-HAP-Ca | 0.1 | HAP-Ca | Silver nitrate | Water | 0.05 | 400 |
| 2 | 0.3Ag-HAP-Ca | 0.3 | HAP-Ca | Silver nitrate | Water | 0.15 | 400 |
| 3 | 0.5Ag-HAP-Ca | 0.5 | HAP-Ca | Silver nitrate | Water | 0.25 | 400 |
| 4 | 0.8Ag-HAP-Ca | 0.8 | HAP-Ca | Silver nitrate | Water | 0.40 | 400 |
| 5 | 1.6Ag-HAP-Ca | 1.6 | HAP-Ca | Silver nitrate | Water | 0.75 | 400 |
| 6 | 0.8Ag-HAP-Sr | 0.8 | HAP-Sr | Silver nitrate | Water | 0.40 | 400 |
| 7 | 0.8Ag-HAP-Mg | 0.8 | HAP-Mg | Silver nitrate | Water | 0.40 | 400 |
| 8 | 0.8Ag-HAP-Ba | 0.8 | HAP-Ba | Silver nitrate | Water | 0.40 | 400 |
| 9 | 0.8Ag-HAP-Pb | 0.8 | HAP-Pb | Silver nitrate | Water | 0.40 | 400 |
| 10 | 0.8Ag-HAP-Ca/Sr | 0.8 | HAP-Ca/Sr | Silver nitrate | Water | 0.40 | 400 |
| 11 | 0.5Co-HAP-Ca | 0.5 | HAP-Ca | Cobalt nitrate | Water | 0.25 | 400 |
| 12 | 0.5Ni-HAP-Ca | 0.5 | HAP-Ca | Nickel nitrate | Water | 0.25 | 400 |
| 13 | 0.5Zn-HAP-Ca | 0.5 | HAP-Ca | Zinc nitrate | Water | 0.25 | 400 |
| 14 | 0.5Cu-HAP-Ca | 0.5 | HAP-Ca | Copper nitrate | Water | 0.25 | 400 |

TABLE 2-continued

Corresponding Relation between Sample Numbers and Preparation Conditions in Embodiment 2

| No. | Catalyst | Metal/ wt % | Carrier | Metal Salt | Solvent | Concentration/ g $mL^{-1}$ | Reduction Temperature |
|---|---|---|---|---|---|---|---|
| 15 | 0.25Cu0.25Ag-HAP-Ca | 0.5 | HAP-Ca | Copper nitrate + silver nitrate | Water | 0.5 | 400 |
| 16 | 0.5Cu-HAP-Ca + 0.5Ag-HAP-Ca | 0.5 | HAP-Ca | Copper nitrate + silver nitrate | Water | 0.5 | 400 |

Embodiment 3

Effect of Partial Pressures of Methanol, Ethanol and Acetone for HAP-Ca Catalyst on Selectivity of Methylphenol.

Methanol, ethanol and acetone as reactants are subjected to coupling-aromatization reaction in a fix bed reactor. Reaction conditions are as follows: the catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, the total partial pressure of methanol and ethanol is 6 kPa, the partial pressure of acetone is 1 kPa, the ratio of the partial pressures of methanol, ethanol and acetone is (1-5):(1-5):1, and the partial pressures of the reactants are adjusted by adjusting the feed flow of methanol, ethanol and acetone. After the reaction is steady, the reaction materials and products are analyzed by on-line chromatogram. The conversion rates of methanol and ethanol and the selectivity of methylphenol at different partial pressures are shown in Table 3, and the selectivity of acetone is close to 100% which is not listed in Table 3.

TABLE 3

Effect of Relative Partial Pressures of Methanol and Ethanol on Selectivity of Methylphenol in Embodiment 3

| Methanol (kPa) | Ethanol (kPa) | Acetone/% (kPa) | Methanol Conversion Rate/% | Ethanol Conversion Rate/% | Methyl-phenol Selec-tivity/% |
|---|---|---|---|---|---|
| 1 | 5 | 1 | 14.9 | 33.5 | 2.6 |
| 2 | 4 | 1 | 18.5 | 29.5 | 2.2 |
| 3 | 3 | 1 | 17.4 | 32.3 | 2.3 |
| 4 | 2 | 1 | 20.8 | 33.8 | 15.8 |
| 5 | 1 | 1 | 23.6 | 33.8 | 6.4 |

Embodiment 4

Effect of Relative Partial Pressure of Acetone for HAP-Ca Catalyst on Selectivity of Methylphenol.

Methanol, ethanol and acetone as reactants are subjected to coupling-aromatization reaction in a fix bed reactor. Reaction conditions are as follows: the catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, the partial pressure of methanol is 4 kPa, the partial pressure of ethanol is 2 kPa, the partial pressure of acetone is adjusted between 0.33 kPa and 3 kPa and adjusted by changing the feed flow of acetone, and the ratio of the partial pressures of methanol, ethanol and acetone is (1.33-12.12):(0.67-6.06):1. The conversion rates of methanol and ethanol and the selectivity of methylphenol at different partial pressures of acetone are shown in Table 4. The selectivity of acetone is close to 100% which is not listed in Table 4.

TABLE 4

Effect of Relative Partial Pressure of Acetone on Selectivity of Methylphenol in Embodiment 4

| Methanol (kPa) | Ethanol (kPa) | Acetone (kPa) | Methanol Conversion Rate/% | Ethanol Conversion Rate/% | Methyl-phenol Selec-tivity/% |
|---|---|---|---|---|---|
| 4 | 2 | 0.33 | 13.1 | 24.7 | 1.3 |
| 4 | 2 | 0.66 | 17.1 | 27.5 | 1.0 |
| 4 | 2 | 1 | 20.8 | 33.8 | 17.2 |
| 4 | 2 | 1.5 | 22.3 | 32.2 | 21.6 |
| 4 | 2 | 2 | 24.3 | 33.8 | 28.3 |
| 4 | 2 | 3 | 25.7 | 37.5 | 25.4 |

Embodiment 5

Catalytic Conversion Performance of xMetal-HAP-M Catalyst.

Methanol, ethanol and acetone as reactants are subjected to coupling-aromatization reaction in a fix bed reactor. Reaction conditions are as follows: the catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, the partial pressure of methanol is 4 kPa, the partial pressure of ethanol is 2 kPa, the partial pressure of acetone is 1 kPa, and the ratio of the partial pressures of methanol, ethanol and acetone is 4:2:1. Different xMetal-HAP-M materials are used as catalysts for the reaction, and the preparation method for the xMetal-HAP-M catalyst is shown in embodiment 2. The conversion rates of methanol and ethanol and the selectivity of methylphenol for different catalysts are shown in Table 5. The selectivity of acetone is close to 100% which is not listed in Table 5.

TABLE 5

Catalysis Performance of Different xMetal-HAP-M Catalysts in Embodiment 5

| No. | Catalyst | Methanol Conversion Rate/% | Ethanol Conversion Rate/% | Methyl-phenol Selec-tivity/% |
|---|---|---|---|---|
| 1 | 0.1Ag-HAP-Ca | 22.5 | 35.1 | 17.5 |
| 2 | 0.3Ag-HAP-Ca | 25.0 | 37.1 | 23.4 |
| 3 | 0.5Ag-HAP-Ca | 27.1 | 32.9 | 28.5 |
| 4 | 0.8Ag-HAP-Ca | 33.9 | 27.9 | 34.0 |
| 5 | 1.6Ag-HAP-Ca | 35.1 | 33.2 | 32.0 |
| 6 | 0.8Ag-HAP-Sr | 22.3 | 32.2 | 21.6 |
| 7 | 0.8Ag-HAP-Mg | 17.0 | 25.1 | 12.1 |
| 8 | 0.8Ag-HAP-Ba | 19.7 | 23.3 | 13.2 |
| 9 | 0.8Ag-HAP-Pb | 15.0 | 20.1 | 10.1 |
| 10 | 0.8Ag-HAP-Ca/Sr | 14.0 | 24.7 | 15.1 |
| 11 | 0.5Co-HAP-Ca | 21.0 | 27.0 | 3.0 |
| 12 | 0.5Ni-HAP-Ca | 29.2 | 40.2 | 14.9 |
| 13 | 0.5Zn-HAP-Ca | 21.6 | 30.5 | 15.6 |
| 14 | 0.5Cu-HAP-Ca | 17.4 | 20.7 | 21.1 |

TABLE 5-continued

Catalysis Performance of Different xMetal-HAP-M Catalysts in Embodiment 5

| No. | Catalyst | Methanol Conversion Rate/% | Ethanol Conversion Rate/% | Methyl-phenol Selec-tivity/% |
|---|---|---|---|---|
| 15 | 0.25Cu0.25Ag-HAP-Ca | 20.3 | 33.7 | 26.5 |
| 16 | 0.5Cu-HAP-Ca + 0.5Ag-HAP-Ca | 21.2 | 32.5 | 27.6 |

Reference Example 1

Product Distribution During Separate Feeding of Methanol, Ethanol and Acetone for HAP-Ca Catalyst.

Methanol, ethanol and acetone as reactants are subjected to catalytic reaction testing in a fix bed reactor. Reaction conditions are as follows: the catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, and the partial pressures of ethanol, methanol and acetone are all 6 kPa. The product distribution during the reaction of different reactants is shown in Table 6.

TABLE 6

Selectivity of Products Corresponding to Different Reaction Substrates in Reference Example 1

| Reactant | Temperature/° C. | Conversion Rate/% | Product Selectivity/% | | | | | | | |
|---|---|---|---|---|---|---|---|---|---|---|
| | | | Dimethyl ether | n-butanol | $C_{6-12}$ alcohol | Mesityl oxide | Isophorone | Trimethyl-benzene | $C_{10+}$ | Methyl phenol |
| Methanol | 300 | 1.1 | 100 | | | | | | | ~0 |
| Ethanol | 300 | 7.5 | | 75.8 | 13.2 | | | | | ~0 |
| Acetone | 300 | 75.2 | | | | 5.5 | 12.3 | 13.5 | 67.5 | ~0 |

Note:

The $C_{10+}$ product is a high molecular weight product of low polymerization of acetone.

As shown in Table 6, when raw materials are fed separately in the reaction, the product distribution of the three substrates is different, and the products do not contain methylphenol, which indicates that methylphenol cannot be obtained by separate feeding at low temperature.

Reference Example 2

Effect of Mixed Feeding of Methanol, Ethanol and Acetone in Pairs for HAP-Ca Catalyst on Selectivity of Methylphenol.

Methanol, ethanol and acetone mixedly fed in pairs are subjected to catalytic reaction testing in a fix bed reactor. Reaction conditions are as follows: the catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, and the conversion rates of methanol and ethanol and the selectivity of methylphenol under different reactant feeding are shown in Table 7.

TABLE 7

Effect of Different Reactant Feeding on Selectivity of Methylphenol in Reference Example 2

| Methanol (kPa) | Ethanol (kPa) | Acetone (kPa) | Methanol Conversion Rate/% | Ethanol Conversion Rate/% | Methylphenol Selectivity/% |
|---|---|---|---|---|---|
| 4 | 2 | 0 | 9.3 | 25.0 | 0 |
| 6 | 0 | 1 | 19.9 | — | 2.6 |
| 0 | 6 | 1 | — | 28.2 | 0.4 |

As shown in Table 7, when methanol and ethanol are fed in a mixed manner, only aliphatic alcohols are produced, and no methylphenol is detected. When acetone is fed together with methanol and ethanol respectively in a mixed manner, only a small amount of methylphenol is detected in the product, which indicates that acetone exists as a substrate that can form cresol, but methylphenol can be produced in a large amount only when three substrates are cross-coupled.

Reference Example 3

Effect of Other Acid-Base Catalysts on Selectivity of Methylphenol During Common Feeding of Methanol, Ethanol and Acetone.

Methanol, ethanol and acetone as reactants are subjected to coupling-aromatization reaction in a fix bed reactor. Catalytic reaction testing is carried out in the fix bed reactor. Reaction conditions are as follows: 200 mg of catalyst is filled in a fix bed reactor with an inner diameter of 8 mm at normal pressure and reaction temperature of 300° C., the weight hourly space velocity is 1 $h^{-1}$, the total flow of the reaction gas is 30 mL/min, the partial pressure of methanol is 4 kPa, the partial pressure of ethanol is 2 kPa, the partial pressure of acetone is 1 kPa, and the ratio of the partial pressures of methanol, ethanol and acetone is 4:2:1. The conversion rates of methanol and ethanol and the selectivity of methylphenol under different catalysts are shown in Table 8.

TABLE 8

Catalytic Performance of Different Acid-Base Catalysts in Reference Example 3

| Catalyst | Temperature/° C. | Methanol Conversion Rate/% | Ethanol Conversion Rate/% | Product Selectivity/% Aliphatic alcohol | $C_{6-12}$ ketone | $C_6$ ring | Alkene | Arene | Ethers | Methylphenol |
|---|---|---|---|---|---|---|---|---|---|---|
| None | 300 | 0 | 0 | | | | | | | ~0 |
| MgAlO | 300 | 16.2 | 15.3 | 40.2 | 10.7 | 2.4 | 5.0 | | | ~0 |
| Co—MgAlO | 300 | 25.6 | 32.6 | 43.7 | 23.3 | 9.6 | 6.4 | | | ~0 |
| Beta zeolite | 300 | 100 | 100 | | | | 5.4 | 44.9 | | 0.5 |
| $Al_2O_3$ | 300 | 87.5 | 79.3 | | | | 100 | | | ~0 |
| $SiO_2$ | 300 | 14.5 | 22.5 | | | | 87.6 | | 12.4 | ~0 |

Note:

The $C_6$ ring includes cyclohexanol, cyclohexanone, cyclohexene ketone and other oxygen-containing intermediates containing six-membered rings.

As shown in Table 8, no reaction occurs in the absence of a catalyst. When other recognized acid-base catalysts are used, high carbon alcohol, alkene and high carbon ketone are more inclined to form in the products due to mismatch of acid-base sites, so the hydroxyphosphate catalyst is preferred in the reaction.

The invention claimed is:

1. A preparation method for methylphenol and its homologue, comprising the following steps:

under the conditions of a reaction temperature of 150-350° C. and a reaction pressure of 1-50 atm, a mixed material of methanol, ethanol and acetone is fed into a reactor containing a catalyst by a carrier gas at a total flow of a reaction gas at 20-200 mL/min to produce methylphenol through a coupling-aromatization reaction.

2. The preparation method according to claim 1, wherein the partial pressure of methanol, ethanol and acetone are 0.1-10 kPa, and the weight hourly space velocity of the reaction is 0.01-3 $h^{-1}$.

3. The preparation method according to claim 2, wherein the ratio of partial pressures of methanol, ethanol and acetone is (0.5-40):(0.5-40):1, the total flow of the reaction gas is 30 ml/min, and the weight hourly space velocity of the reaction is 0.2-1.5 $h^{-1}$.

4. The preparation method according to claim 1, wherein the carrier gas is nitrogen, argon or helium.

5. The preparation method according to claim 1, wherein the catalyst is a mixture of a hydroxyphosphate catalyst and/or a hydroxyphosphate catalyst modified by a transition metal.

6. The preparation method according to claim 5, wherein the chemical formula of the hydroxyphosphate catalyst is $A_xB_yC_zD_mE_n(OH)_2(PO_4)_6$, wherein x+y+z+m+n=9-10, 9-10≥x, y, z, m, n≥0, A, B, C, D and E are the same or different, and are selected from one or a combination of more than one of Mg, Ca, Sr, Ba and Pb, and the hydroxyphosphate catalyst is one or a mechanical mixture of more than one.

7. The preparation method according to claim 6, wherein the hydroxyphosphate catalyst is $Ca_{10}(OH)_2(PO_4)_6$.

8. The preparation method according to claim 5, wherein the transition metal comprises a non-noble metal and/or a noble metal; the non-noble metal is selected from one or a combination of more than one of Co, Ni, Cu, Zn and Y; the noble metal is selected from one or a combination of more than one of Ag, Pt and Ir; the transition metal is in an oxidation state or metallic state; and the transition metal uses nitrate, chloride, levulinate, sulfate or acetate of the metal as a precursor, the concentration of a precursor solution is 0.05 g/mL-0.75 g/mL, and a modification amount of the transition metal is 0.01-50 wt % of the weight of the hydroxyphosphate catalyst.

9. The preparation method according to claim 8, wherein the transition metal is Ag and Cu, and the modification amount is 0.1-10 wt % of the hydroxyphosphate catalyst.

10. The preparation method according to claim 5, wherein the hydroxyphosphate catalyst modified by the transition metal is reduced for 1-5 h at 350-750° C. in hydrogen atmosphere before the reaction, and a concentration of the hydrogen atmosphere is one of 5-30 vol % $H_2/N_2$, 5-30 vol % $H_2$/He and 5-30 vol % $H_2$/Ar.

* * * * *